United States Patent
Rego et al.

(10) Patent No.: US 10,758,480 B2
(45) Date of Patent: Sep. 1, 2020

(54) POLYIODIDE RESIN POWDER FOR USE WITH MEDICAL DEVICES

(71) Applicant: Valencide LLC, San Diego, CA (US)

(72) Inventors: Albert Rego, Mission Viejo, CA (US); Lynn R. Detlor, Ramona, CA (US)

(73) Assignee: VALENCIDE LLC CA (US)

( * ) Notice: Subject to any disclaimer, the term of this patent is extended or adjusted under 35 U.S.C. 154(b) by 0 days.

(21) Appl. No.: 16/844,967

(22) Filed: Apr. 9, 2020

(65) Prior Publication Data

US 2020/0246260 A1 Aug. 6, 2020

Related U.S. Application Data

(63) Continuation-in-part of application No. 15/711,424, filed on Sep. 21, 2017, now Pat. No. 10,709,819.

(51) Int. Cl.
| | | |
|---|---|---|
| *A61K 33/18* | (2006.01) | |
| *A61K 9/00* | (2006.01) | |
| *A61M 16/00* | (2006.01) | |
| *A61M 16/14* | (2006.01) | |
| *A61M 15/00* | (2006.01) | |

(52) U.S. Cl.
CPC .......... *A61K 9/0078* (2013.01); *A61K 9/0075* (2013.01); *A61K 33/18* (2013.01); *A61M 15/00* (2013.01); *A61M 16/0057* (2013.01); *A61M 16/14* (2013.01); *A61M 2202/064* (2013.01)

(58) Field of Classification Search
CPC .................................................... A61K 33/18
See application file for complete search history.

(56) References Cited

U.S. PATENT DOCUMENTS

| | | | |
|---|---|---|---|
| 4,010,259 A | 3/1977 | Johansson | |
| 4,381,380 A | 4/1983 | LeVeen et al. | |
| 4,999,190 A * | 3/1991 | Fina ........................ | A01N 59/12 |
| | | | 424/497 |

FOREIGN PATENT DOCUMENTS

| | | |
|---|---|---|
| WO | WO 2010033258 A1 | 3/2010 |
| WO | WO 2010124130 A2 | 10/2010 |

OTHER PUBLICATIONS

Luo et al., "Antimicrobial Activity and Biocompatibility of Polyurethane-Iodine Complexes." Journal of Bioactive and Compatible Polymers, vol. 25, No. 2, Mar. 2010, pp. 185-206.

* cited by examiner

*Primary Examiner* — Benjamin J Packard
(74) *Attorney, Agent, or Firm* — Aileen Law; Oppedahl Patent Law Firm LLC

(57) ABSTRACT

Disclosed is a system and method of treatment which provides a direct response to the treatment of pneumonia as related to infections using a powder comprising a polyiodide resin with broad spectrum bactericidal, fungicidal and virucidal properties. When the powder is applied directly to the lungs of a mammal an immediate contact kill of protozoa, bacteria, fungi and viruses that cause respiratory tract infections affecting the lungs of a mammal takes place.

| Wuxi Apptec Laboratory Reports | Pseudomonas[1] aeruginosa – Log Reduction | Staphylococcus aureus- Log Reduction | Contact times |
|---|---|---|---|
| Final Report 824050.pdf | > 6.0 | | 0, 5 (min.) |
| Final Report 823395 (2).pdf | > 5.9 | > 4.6 – 6.2 | 0, 2, 5, 15 (min.) |
| Final Report 822668.pdf | > 6.5 | > 5.0 | 0, 2, 5, 15 (min.) |
| 901978.pdf | > 6.3 | | 0, 24, 48, 72, 96 (hrs.) |
| 831569.pdf | > 6.1 | | 0, 72 (hrs.) |
| 829684 | > 5.6 | | 0, 2, 5, 15 (min.) |
| 823213.pdf | > 4.3 | | 0, 24 (hrs.) |
| 793489.pdf | > 2.3, 5.0, 6.6, 6.2 | > 4.4, 5.1, 6.0, 6.2 | 0, 24, 48, 72 (hrs.) |

[1]Pseudomonas aeruginosa is considered an excellent model for evaluation of efficacy due to its ruggedness and its resistance to antimicrobial agents.

POLYIODIDE RESIN POWDER FOR USE WITH MEDICAL DEVICES

TECHNICAL FIELD

The present disclosure relates to an agent comprising polyiodide resin for use with delivery devices such as DPIs (Dry Product Inhalers), nebulizers or ventilators, and the like to provide an immediate contact kill of bacteria, fungi and viruses. More specifically, the present device provides for a bactericidal, fungicidal and virucidal agent for infections such as tuberculosis, "SARS" caused by the SARS-coronavirus (SARS-CoV or SARS-CoV-1), "MERS" caused by the MERS-coronavirus (MERS-CoV) and "COVID-19" caused by the SARS-coronavirus (SARS-CoV-2), influenza viruses and ebolaviruses affecting the lungs of a mammal.

BACKGROUND

Iodine is a well-known broad spectrum antimicrobial agent that has bactericidal, fungicidal and virucidal properties which has been used for over centuries as an antiseptic. When iodine is introduced into an aqueous solution, free iodine, which provides the germicidal effect, is released. While generally inhibiting infective germs over the short term, the biocidal effectiveness of iodine is dependent on, inter alia, how long the infective agent is exposed to it.

To increase the effectiveness of iodine, it is normally combined with a solubilizing agent or other carrier to form an iodophor. Such iodophors, in effect, provide a reservoir of iodine from which small amounts of free iodine in aqueous solution are released over a period of time. This iodophor formulated for example, as a solution, soap, cream or paste, and are then topically applied to that area of a patient's body which is desired to be treated. Perhaps the best known of these iodophors is povidone-iodine, in which iodine in the form of triiodide is complexed with the polymer polyvinylpyrrolidone. An example of such an application can be found by reference to U.S. Pat. No. 4,010,259.

Polyiodide resins have proven to be as much as 1,000,000 times more effective than an iodine ($I_2$) molecule alone. A large number of chemical, biochemical, and physiological studies have proven that the iodine added to microorganisms is irreversibly bound. This has the effect of devitalizing the microorganisms by damaging cellular proteins, lipids, enzymes, oxidation of sulfhydryl groups and other chemical pathways Microorganisms carry an electrical potential energy on their surface. The polyiodide resin carries an electrical potential charge which attracts the microorganisms. The microorganisms with their negative electrical potential are naturally drawn to the iodinated resin particles with their positive electrical potential charge and vice versa, thus ensuring contact and devitalization. The iodinated resin releases the correct lethal dose of nascent iodine in less than about 3 seconds at a body temperature of about 98.6° C. or about 36.9° C.

The ion-exchange resin bead or particle is chemically bonded homogeneously with polyiodide of uniform composition throughout its interior. As nascent iodine is consumed more is continuously fed to the surface from the interior of the resin bead or particle.

The unique release on demand feature of polyiodide resin can be demonstrated by adding resin beads to the well of a depression microscope slide with a suspension of the highly Motile Ciliate Tetrahymena Pyriforms. When observed microscopically, individual cells maintain their motion while swimming in a solution with 2 ppm of iodine residual. However after a collision with a resin bead, their activity dramatically slows and within seconds stops altogether.

Bacteria, viruses, yeast, fungi, and protozoa are not able to develop resistance to iodine even after a period of prolonged exposure to polyiodinated resins. It is not expected that emerging new infections will develop resistance to iodine, as historically there has been no development of resistance to iodine, as well as polyiodinated resin.

SUMMARY OF THE DISCLOSURE

The disclosed device provides for a treatment for various forms of pneumonia in mammals originating from bacterial, fungal and viral agents through the application of a powder form of polyiodide resin.

The disclosed system provides for treatment of pneumonia in the lungs of a mammal with via a broad spectrum antimicrobial agent that has bactericidal, fungicidal and virucidal properties comprising polyiodide resin.

The disclosed system provides for direct contact kill of organisms in the lungs of a mammal.

The disclosed system provides for very broad spectrum viral, bacterial, fungicidal antimicrobial effectiveness for treatment of bacteria, viruses, yeast, fungi, and protozoa.

The disclosed system provides for a sustained kill of organisms for up to 96 hours.

The disclosed system can provide for treatment of a mammalian patient entailing one application for effectiveness.

The disclosed system provides for treatment of a mammalian patient requiring one or more applications as needed.

The disclosed device comprises an agent (polyiodide resin powder) used with a delivery device such as a DPI (Dry Product Inhaler), nebulizer or ventilator to provide an immediate contact kill of bacteria, fungi and viruses causing respiratory tract infections affecting the lungs of a mammal.

The disclosed device is applicable to but not limited to treating various forms of respiratory tract infections, e.g., pneumonia caused by cornaviruses such as SARS-CoV-1, SARS-CoV-2, MERS-CoV, influenza viruses such as SIV or S-OIV and ebolaviruses such as EBOV.

BRIEF DESCRIPTION OF THE FIGURES

FIG. 4 Table of compiled data exhibiting contact times and effectiveness.

DETAILED DESCRIPTION OF THE DISCLOSURE

Definitions

Figure 1:
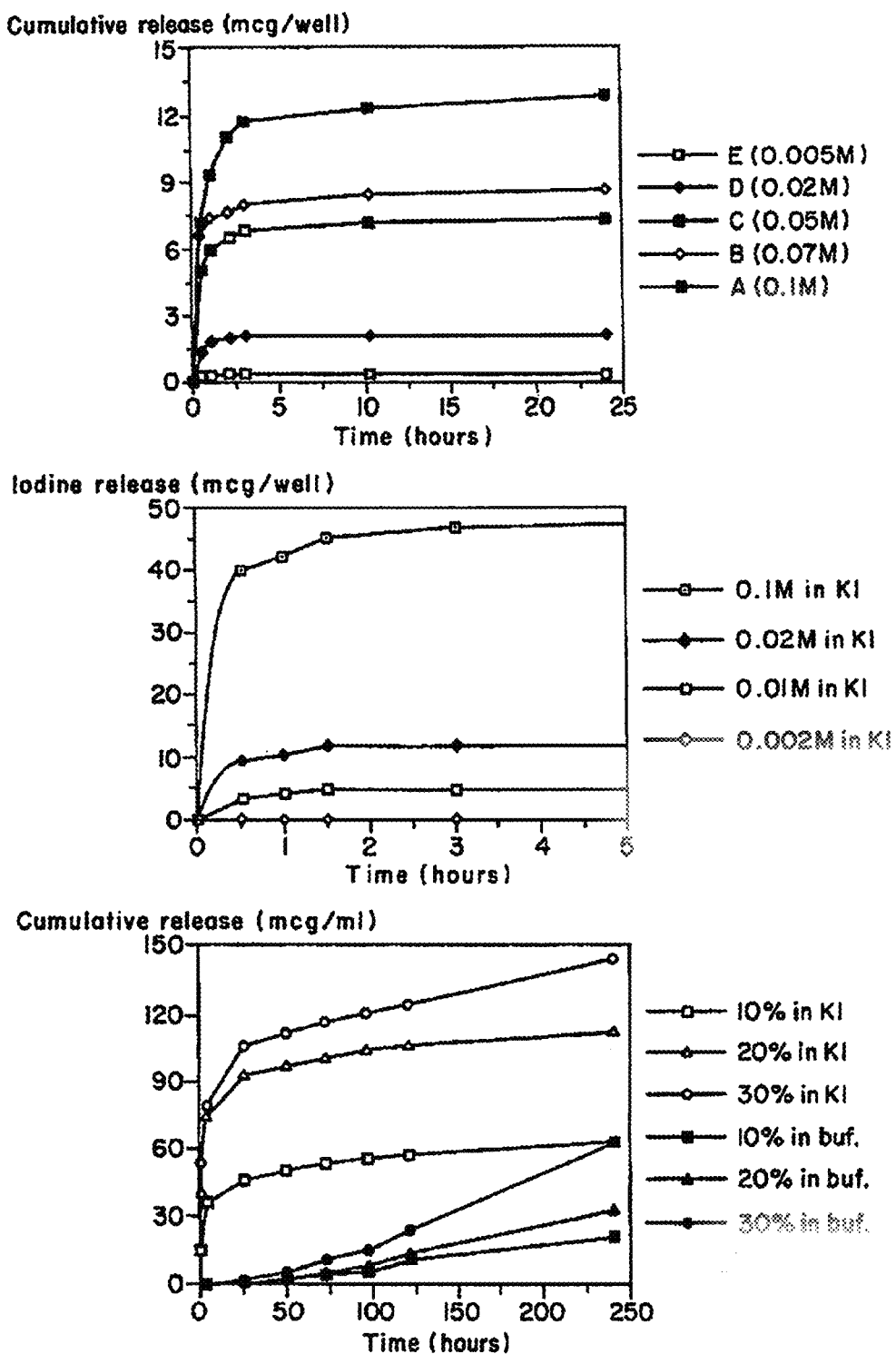
FIG. 1. Release rates from previous studies.
Figure 2:
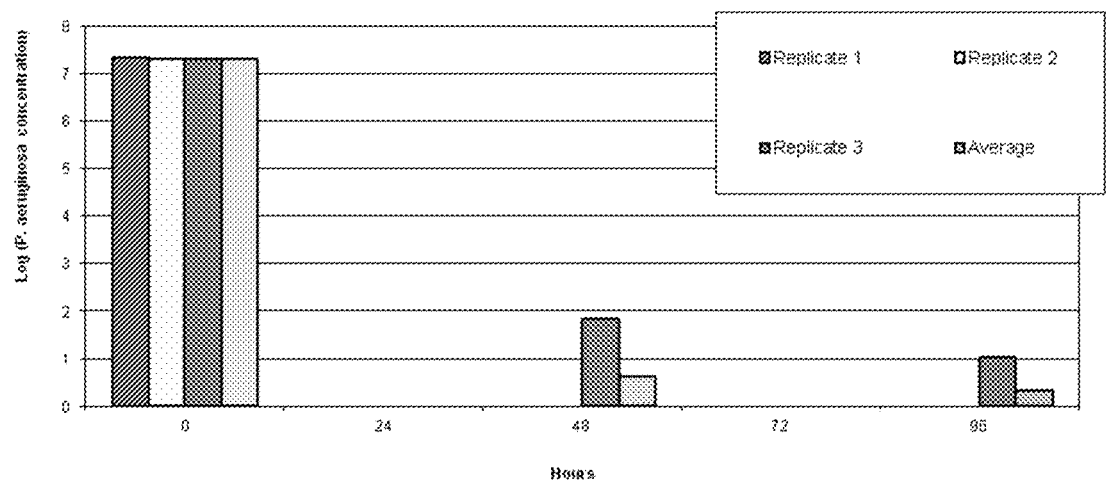
FIG. 2 Graph showing biological performance of latex/iodinated resin coated latex elastomers of the present disclosure against the challenge microorganism *Pseudomonas aeruginosa*, with re-inoculation every twenty-four hours (Report Number 901978).
Figure 3:
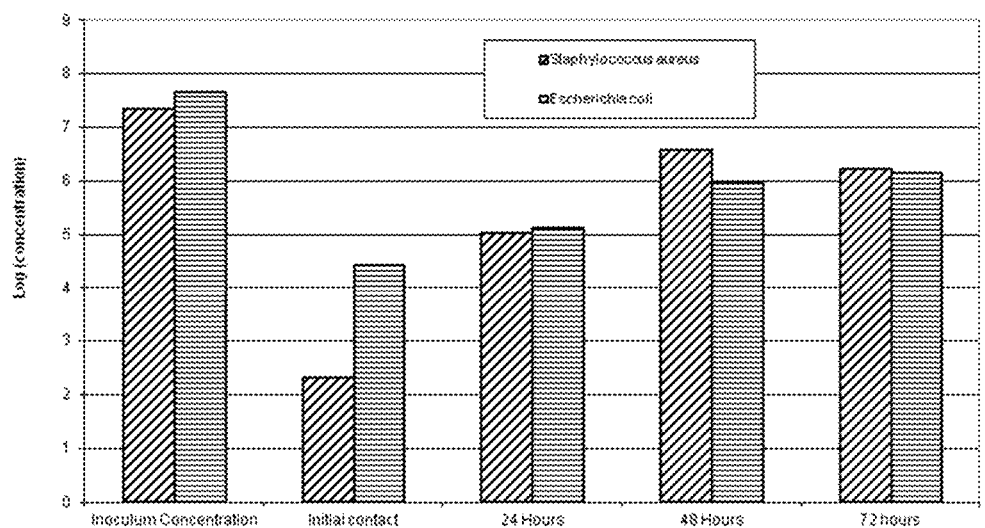
FIG. 3 Graph showing biological performance of latex/iodinated resin coated latex elastomers of the present disclosure against the challenge microorganisms *S. aureus* and *E. Coli* (Report Number 793489).

Polyiodide—Molecular iodide of more than one iodine atom containing a net negative charge Antimicrobial—An agent that kills microorganisms or inhibits their growth.

Ion-Exchange—An exchange of ions between two electrolytes or the exchange of ions of the same charge between an insoluble solid and a solution in contact with it or an electrolyte solution and a complex or solid state material. Biological Buffer—An organic substance that has a neutralizing effect on hydrogen ions.

The antitoxic agent is preferably an antimicrobial agent, an antiviral agent, a biochemical agent or a reducing agent. The active agent preferably exerts a toxic effect on a diverse array of microorganisms and other pathogens and environmental toxins while not being toxic to the user. Preferably, the antitoxic agent comprises polyiodinated resin particles.

Disinfectants are known in the art. One preferred demand disinfectant is polyiodinated resins. The particle sizes of the powders range from about 1 micron to about 150 microns. Preferably, the particle sizes should be in the range from about 5 microns to about 10 microns. Alternative sources of the polyiodinated resins may be used subject to meeting the same purity and physical conditions. Iodinated resins used in accordance with the present disclosure are referred to as polyiodinated resin.

The base polymer used to manufacture such polyiodinated resins is a strong base anion exchange resin. These resins contain quaternary ammonium exchange groups which are bonded to styrene divinylbenzene polymer chains. Polyiodinated resins can be made with different percentages of iodine and may be used in accordance with the present disclosure. Different percentages of iodine in the polyiodinated resins will confer different properties to the resin, in particular, different levels of biocidal activity. The particular resin used is based on the desired application.

A significant advantage of the present disclosure is that a relatively small amount of the antimicrobial agent need be applied in order to exert a significant toxic effect on a broad spectrum of pathogens.

With regards to efficacy, the present disclosure has been tested against a robust organism *Pseudomonas aeruginosa* utilizing the following recognized standards: AATCC Method 100 (modified for twenty four hour repeat insult testing) and ASTM E2149 (modified for twenty four hour repeat insult testing). The test results showed an average reduction of greater than $10^6$ in bacterial count vs. untreated samples).

With regards to efficacy, the present disclosure has been tested against a robust organism *Staphylococcus aureus* utilizing the following recognized standards: AATCC Method 100 (modified for twenty four hour repeat insult testing). The test results showed an average reduction of greater than $10^6$ in bacterial count vs. untreated samples).

As an example, a horse having late stage pneumonia that was expected to expire within 24 hours was treated with the disclosed dry powder and was within 24 hours healthy and pneumonia free.

The polyiodide resin powder when applied to the lungs of a mammal via a DPI, nebulizer or ventilator the antimicrobial agent is released.

One disclosed embodiment is a powder demand release antimicrobial contact disinfectant polyiodinated resin with the ability to be tailored to specific medical needs based on the iodine concentration of iodine in its various forms such as $I_3^-$, $I_5^-$, $I_7^-$.

The powder demand release antimicrobial contact disinfectant polyiodinated resin has been proven to maintain its kill capabilities beyond 96 hours (repeated inoculation every 24 hours with >10⁷ *Pseudomonas aeruginosa* for the entire study) as referenced by test results done by Wuxi AppTec, a third party reference lab. The antimicrobial powder is capable of providing a high level of protection against microbes and other many biohazards, such as viruses, bacteria, fungi, and molds. In the disclosed embodiment, the polyiodinated resin particles advantageously have an average size within the range from about 5 μm to about 10 μm.

As disclosed, the polyiodide resin powder begins with a pure cationic resin which is commercially available as a chloride ($Cl^-$) as the anion. The anion exchange resin may be a whole series of possible polymers that are carbon based, but in the disclosed embodiment, the resin used is a commercially available styrenedivinylbenzene copolymer resin that has a quaternary ammonium cation as an integral part of the resin matrix. This can be described as resin with nitrogen (N) and carbon-based residues (R) attached to the resin, with the property of having a resin with a positive charge and a counter anion ($Cl^-$) with a negative charge, to end up as a neutral complex.

Typically, anion exchange resins are in the form of hydroxide ($OH^-$) or chloride (Cl–). The hydroxide form can be further reacted with hydrochloric acid to form the chloride version of the resin as follows:

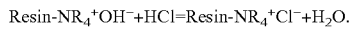
$$\text{Resin-}NR_4^+OH^- + HCl = \text{Resin-}NR_4^+Cl^- + H_2O.$$

This is further reacted in the presence of Iodine ($I_2$ as a mineral) and Iodide ($I^-$) salt (sodium or potassium iodide) to allow for the formation of $I_3^-$, $I_5^-$, and $I_7^-$. The initial reaction is $[I_2+I^-=I_3^-]$, which upon excess $I_2$ will react further to form $I_5-$ as in $[I_2+I_3^-=I_5^-]$, and which upon additional excess $I_2$ will react further to form $I_7-$ as in $[I_2+I_5^-=I_7^-]$. This is now referred to as the polyiodide resin in the disclosed system. Reactions are as follows:

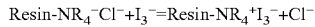
$$\text{Resin-}NR_4^-Cl^- + I_3^- = \text{Resin-}NR_4^+I_3^- + Cl^-$$

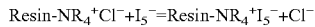
$$\text{Resin-}NR_4^+Cl^- + I_5^- = \text{Resin-}NR_4^+I_5^- + Cl^-$$

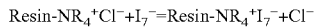
$$\text{Resin-}NR_4^+Cl^- + I_7^- = \text{Resin-}NR_4^+I_7^- + Cl^-$$

Various ratios of chemicals are combined to optimize the formation of the polyiodide versions above by adding an excess of the $I_2$ and $I^-$ in appropriate proportions to substitute out the $Cl^-$ based on the stoichiometry (ratio) of the reactants as given above. Multiple routes from chromatography to reactor pressures and heated fluid beds may be used to realize the end product in accordance with well-known manufacturing processes, with the variables of pressure, temperature and ratios.

The reactor operates at elevated temperatures of above room temperature to the limits of the resin's thermal stability profile temperature and at pressures of one or more atmospheres of pressure. The process can be optimized to produce a batch of any size (subject to the reactor vessel size) in a matter of hours or within one day. The total weight of iodine in the polyiodinated resin formed from the process ranges about 45% to about 70% by weight of the polyiodide complex depending on the introduction of $I_3^-$, $I_5^-$, and/or $I_7^-$. By careful control of the ratios of the Resin based Chloride version of the resin and the $I_2$ and $I^-$ ratios, mixtures ranging from the $I_3^-$ through the $I_7^-$ versions and mixtures in between can be produced. Careful control of specific ratios of reactants can yield specific versions, but are typically reaction mixtures favoring one of the polyiodides over the others. For example, if $I_3^-$ is introduced, the resulting polyiodinated resin comprises about 45% by weight of the polyiodide complex. If $I_5^-$ is introduced, the resulting polyiodinated resin comprises about 62% (by weight of the polyiodide complex. If $I_7^-$ is introduced, the resulting polyiodinated resin comprises about 69% by weight of the polyiodide complex.

The resulting polyiodide resin is then ground to about 5 μm to about 10 μm thereby forming the polyiodide resin powder. Yields at or near 100% are possible, but typically due to manufacturing loses and limits may be less than 100%.

Buffering agent can be added to maintain the desired pH, subject to the specific buffering agent that is used, in a ratio that allows for the control of the pH of the mixture in a wet environment (such as tissue or lungs) to be in the range of 3 to 7 pH units. Although any ratio of polyiodide to buffering agent can be used in the range of 10% to 100% of the polyiodide, typically the dominate agent is the polyiodide in the range of 50% to 100% of the total of the combined materials of the polyiodide styrene divinylbenzene copolymer resin and the buffer agent.

Some examples for medical grade buffering agents that may be used are 4-(2-hydroxyethyl)-1-piperazineethanesulfonic acid (HEPES), 2-(N-morpholino)ethanesulfonic acid (MES), 3-(N-morpholino)propanesulfonic acid (MOPS) and citrates, however others may be suitable.

The invention claimed is:

1. A treatment system for use with a medical delivery device to provide an immediate contact kill of bacteria, fungi and viruses that cause respiratory tract infections affecting the lungs of a mammal, the system comprising:
 a polyiodide resin powder comprising a cationic resin having an anion that when reacted in the presence of iodine ($I_2$ as a mineral) and Iodide ($I^-$) salt (sodium or potassium iodide) forms $I_3^-$, $I_5^-$, and $I_7^-$;
 the polyiodide resin powder having a total weight of iodine ranging from about 45% to about 70% by weight of polyiodide complex depending on the introduction of $I_3^-$, $I_5^-$, and/or $I_7^-$;
 wherein the polyiodide resin powder comprises a mesh size of about 5 μm to about 10 μm; and
 a buffering agent to enable the polyiodide resin powder to be maintained at a desired pH in a ratio that allows for the control of the pH of the mixture in a wet environment.

2. The system of claim 1, wherein the polyiodide resin powder mixture is introduceable into the lungs of a mammal via a delivery device.

3. The system of claim 2, wherein the delivery device comprises a dry product inhaler.

4. The system of claim 2, wherein the delivery device comprises a nebulizer.

5. The system of claim 2, wherein the delivery device comprises a ventilator.

6. The system of claim 1, wherein the pH ranges from about 3 to about 7.

7. The system of claim 1, wherein the ratio of polyiodide to buffering agent ranges from about 50% to about 100% of the total of the combined materials of the cationic resin and the buffering agent.

8. A method for providing a polyiodide resin powder for use with a medical delivery device to enable an immediate contact kill of bacteria, fungi and viruses that cause respiratory tract infections affecting the lungs of a mammal, the method comprising the steps of:
 providing a cationic resin comprising a positive charge and an anion with a negative charge;
 reacting the cationic resin in the presence of iodine ($I_2$ as a mineral) and Iodide ($I^-$) salt (sodium or potassium iodide) to allow for the formation of $I_3^-$, $I_5^-$, and $I_7^-$ thereby forming a polyiodide resin having a total weight of iodine ranging from about 45% to about 70% by weight of polyiodide complex depending on the introduction of $I_3^-$, $I_5^-$, and/or $I_7^-$;
 processing said polyiodide resin to form a polyiodide resin powder having a mesh size of about 5 μm to about 10 μm; and
 adding a buffering agent to enable the pH of the polyiodide resin powder to be maintained in a ratio that allows for the control of the pH of the mixture in a wet environment.

9. The method of claim 8, further comprising the step of introducing the polyiodide resin powder mixture into the lungs of a mammal via a delivery device.

10. The method of claim 9, wherein the delivery device comprises a dry product inhaler.

11. The method of claim 9, wherein the delivery device comprises a nebulizer.

12. The method of claim 9, wherein the delivery device comprises a ventilator.

13. The method of claim 8, wherein the desired pH ranges from about 3 to about 7.

14. The method of claim 8, wherein the ratio of polyiodide to buffering agent ranges from about 50% to about 100% of the total of the combined materials of the cationic resin and the buffering agent.

15. A treatment system for use with a medical delivery device to provide an immediate contact kill of bacteria, fungi and viruses that cause respiratory tract infections affecting the lungs of a mammal, the system comprising:
 a polyiodide resin powder comprising a cationic resin having an anion that when reacted in the presence of iodine ($I_2$ as a mineral) and Iodide ($I^-$) salt (sodium or potassium iodide) forms $I_3^-$, $I_5^-$, and $I_7^-$;
 the polyiodide resin powder having a total weight of iodine ranging from about 45% to about 70% by weight of polyiodide complex depending on the introduction of $I_3^-$, $I_5^-$, and/or $I_7^-$;
 wherein the polyiodide resin powder comprises a mesh size of about 5 μm to about 10 μm; and
 wherein the polyiodide resin powder further comprises a buffer agent added to maintain the pH of the polyiodide resin powder in a wet environment.

16. The system of claim 15, wherein the polyiodide resin powder is introduceable into the lungs of a mammal via a dry product inhaler.

17. The system of claim 15, wherein the polyiodide resin powder is introduceable into the lungs of a mammal via a nebulizer.

18. The system of claim 15, wherein the polyiodide resin powder is introduceable into the lungs of a mammal via a ventilator.

* * * * *